(12) United States Patent
Zikria et al.

(10) Patent No.: US 7,041,655 B1
(45) Date of Patent: May 9, 2006

(54) CAPILLARY MEMBRANE STABILIZATION AND REDUCTION OF TISSUE INJURY THROUGH USE OF IV BIODEGRADABLE MACROMOLECULES WITH ANTIOXIDANTS AND/OR OTHER CHEMICALS

(76) Inventors: Bashir Zikria, 196 Millbrook Cir., Norwood, NJ (US) 07640; Jemal D. Zikria, 196 Millbrook Cir., Norwood, NJ (US) 07640

( * ) Notice: Subject to any disclaimer, the term of this patent is extended or adjusted under 35 U.S.C. 154(b) by 767 days.

(21) Appl. No.: 08/837,840

(22) Filed: Apr. 22, 1997

Related U.S. Application Data

(60) Provisional application No. 60/015,963, filed on Apr. 24, 1996.

(51) Int. Cl.
*A61K 31/715* (2006.01)
*A61K 38/44* (2006.01)

(52) U.S. Cl. .............................. 514/54; 514/59; 514/60; 514/833; 424/94.4; 435/18.3

(58) Field of Classification Search .................. 514/54, 514/59, 60, 833; 424/94.4; 435/183
See application file for complete search history.

(56) References Cited

U.S. PATENT DOCUMENTS 4,994,444 A * 2/1991 Zikria ......................... 514/60

OTHER PUBLICATIONS

Weiss, Stephen J. J. Biol. Chem. 255:20, 9912–9917, 1980.*
Gerdin. et al. Chem. Abstr. No. 99:47701p, p. 34, 1983, Int. J. Microcirc. Clin. Exp. 2(1):39–46, 1983.*
Munkres et al. EMBASE Abstr. No. 8418469, Age, 7(2): 30–35, 1984.*

* cited by examiner

*Primary Examiner*—James O. Wilson
*Assistant Examiner*—Howard V. Owens
(74) *Attorney, Agent, or Firm*—Evelyn M. Sommer

(57) ABSTRACT

In accordance with the invention there is provided a method of treating a human subject to prevent leakage of serum proteins from capillary endothelial junctions during a period of increased capillary permeability. The invention also provides a method for preventing the harmful effects of free radicals on cellular membranes and other organelles. The method comprises administering to a subject an effective amount of a composition comprising at least one polysaccharide selected from the group consisting of hydroxyethyl starch and dextran of varying molecular sizes and at least one member of the group consisting of superoxide dismutase, glutathione peroxidase, catalase, hydroxyethyl rutoside, cyclic adenosine monophosphate and vitamin C. The compositions contain the macromolecules in a molecular size and concentration to effectively stabilize the capillary membrane. The stabilization effect is accomplished by a biophysical/biochemical process due to the adhesiveness and configuration of the macromolecules and because of their size. The treatment is benign as the macromolecules and antioxidants and non-toxic and biodegradable.

20 Claims, No Drawings

CAPILLARY MEMBRANE STABILIZATION AND REDUCTION OF TISSUE INJURY THROUGH USE OF IV BIODEGRADABLE MACROMOLECULES WITH ANTIOXIDANTS AND/OR OTHER CHEMICALS

This application relates to Provisional application Ser. No. 60/015,963 filed Apr. 24, 1996.

The present invention relates to a method for treating human subjects to prevent leakage of macromolecules from capillary endothelial junctions and at the same time preventing damage to the capillaries and surrounding tissues due to the presence of released free radicals. More particularly this invention relates to biophysical and biochemical methods for preventing leakage of macromolecules from capillary endothelial junctions during a period of increased capillary permeability secondary to burn injury, cytotoxicity, trauma, septic and hemorrhagic shock, ischemia and other inflammatory processes and at the same time preventing pathology due to the activity of free radicals.

In accordance with the invention there is provided a method of treating a human subject to prevent leakage of serum proteins from capillary endothelial junctions during a period of increased capillary permeability. The invention also provides a method for preventing the harmful effects of free radicals on cellular membranes and other organelles. The method comprises administering to a subject an effective amount of a composition comprising at least one polysaccharide selected from the group consisting of hydroxyethyl starch and dextran of varying molecular sizes and at least one member of the group consisting of superoxide dismutase, glutathione peroxidase, catalase, hydroxyethyl rutoside, cyclic adenosine monophosphate and vitamin C. The compositions contain the macromolecules in a molecular size and concentration to effectively stabilize the capillary membrane. The stabilization effect is accomplished by a biophysical/biochemical process due to the adhesiveness and configuration of the macromolecules and because of their size. The treatment is benign as the macromolecules and antioxidants are non-toxic and biodegradable.

The compositions of the invention comprise at least one macromolecular polysaccharide selected from the group consisting of hydroxyethyl starch (HES, hetastarch, Hespan®) and dextran and at least one pharmacologically active agents selected from superoxide dismutase (SOD), glutathione peroxidase, catalase, hydroxyethyl rutoside, cyclic adenosine monophosphate (cyclic AMP) and vitamin C.

The protective action of the polysaccharides macromolecules has been shown to be brought about by biophysical and biochemical processes resulting in membrane stabilization of the capillary endothelial cell by virtue of the "sealing" effects of these macromolecules. The protective effects of the antioxidants are due to their activity alone or in combination in neutralizing the harmful effects of free radicals.

Current scientific literature reveals that inflammatory mediators initiate a biochemical chain of events that increase capillary permeability. These mediators include pharmacologically active amines such as histamine and 5-hydroxytryptamine, polypeptides such as bradykinin, kallikrein and leukotoxine, the prostaglandins, and various complements including derivatives thereof. These mediators act specifically on the junction of the endothelial cells of capillaries so that the junctions cannot contain colloids such as serum albumin within the vessel. The serum albumin escapes into the interstitium creating a nonfunctional "third space", the volume of which increases proportionally to albumin leakage and the presence of cytokines as well as proteolytic enzyme activities within the matrix. This leakage further widens capillary membrane-mitochondrial distances creating problems of poor diffusion and transport between the circulatory system and the functional cells resulting in cellular anoxia, a cellular energy deficit, and acidosis, and possibly leading to sequential organ failure.

In the past, the problem of albumin leakage and the concurrent creation of a third space has been approached through pharmacological means. The present invention approaches the problem as a both a biophysical and biochemical phenomenon. The biophysical treatment involves the utilization of natural or synthetic polysaccharides (macromolecules) as capillary membrane stabilizers to prevent or substantially reduce the escape of albumin and other molecules through the junction of the endothelial cells of the capillaries. This is accomplished by virtue of the configuration and physical properties (adhesiveness) of the utilized polysaccharides.

Hydroxyethyl starch (Hespan U.S. Pat. No. 3,523,938) is an artificial colloid derived from a waxy starch, composed almost entirely of amylopectin. The branched amylopectin polymer has a degree of polymerization on the order of several hundred glucose residues. The segments between the branched points average about 25 glucose residues linked by alpha-D-(1-4) glucosidic bonds, while the branched points are linked by alpha-D-(1-6) bonds. Hydroxyethyl ether groups are introduced into the glucose units of the starch and the resultant material is hydrolyzed. Clinical hetastarch is characterized by its molecular weight and its degree of substitution. The average molecular weight is approximately 480,000 daltons with a range of 400,000 to 500,000 and with 80% of its polymer units falling within the range of 30,000 to 2,400,000 daltons. The molar substitution is 0.7 which means hetastarch has 7 hydroxyethyl groups for every 10 glucose units. The polymerized glucose units in hetastarch are joined primarily by 1-4 linkage with hydroxyethyl groups being attached primarily at the number 2 position. The polymer closely resembles glycogen. The degree of branching is approximately 1:20 which means that there is one 1-6 branch for every 20 glucose monomer units. The chemical name for hetastarch is hydroxyethyl starch. The structural formula is as follows:

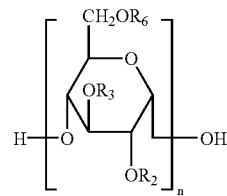

Amylopectin derivative in which $R_2$, $R_3$, and $R_6$ are H or $CH_2CH_2OH$, or $R_6$ is a branching point in the starch polymer connected through a 1-6 linkage to additional α-D-glucopyranosyl units.

The colloidal properties of 6% hetastarch approximate those of human albumin. Intravenous infusion of hetastarch results in expansion of the plasma volume slightly in excess of the volume infused but which decreases over the succeeding 24–36 hours. This expansion of plasma volume improves the hemodynamic status of the subject for 24 hours or longer. Hydroxyethyl starch molecules below 50,000 daltons are rapidly eliminated by renal excretion with approximately 40% of a given total dose appearing in the urine in 24 hours. The hydroxethyl group is not cleaved by the body, but remains intact and attached to the glucose units when excreted. Significant quantities of glucose are not produced (metabolism) as hydroxyethylation prevents complete metabolism. Despite its extensive clinical use hydroxyethyl starch has not been observed to act in a way more than merely exerting a colloidal oncotic pressure when compared to albumin.

Hydroxyethyl starch is administered by intravenous infusion only. In adults the amount usually administered is 30 to 100 grams in solution. Doses of 1500 mls of 6% hydroxyethyl starch per day per 70 kg man have been used in postoperative and trauma patients. Hydroxyethyl starch can be delivered in 0.9% saline, 5% dextrose or Ringer'lactate. A preparation of Hespan® (Dupont) is commercially available as 6% hetastarch in 0.9% NaCl. The osmolarity of this preparation is 310 mOsM/liter.

The inventors have utilized polysaccharides other than hetastarch and have produced promising results. These polysaccharide macromolecules include glycogen and dextran.

Dextran, another polysaccharide is made up of glucose residues only, mainly in alpha-1-6 linkage. Occasional branches are formed by alpha-1-2, alpha-1-3 or alpha-1-4 linkages. The nature of the linkages are dependent on the source of the dextran. Certain bacteria secrete dextran as a by-product of their growth and commercial dextran is manufactured by bacterial culture procedures. By varying the growth conditions of the bacteria, the molecular weight of the dextran can be controlled to bring about the desired size. Useful molecular weights for plasma substitution range from 40,000 to 500,000 daltons. Dextran of appropriate molecular size does not pass through the capillary pores and therefore, can replace plasma proteins as colloid osmotic agents.

Dextran injectable solutions are commercially available. Such preparations include eg. Dextran (Merck) native dextran ($CH_6H_{10}O_5$) with molecular weights in the range of 5,000,000 to 40,000,000. Rheomacrodex® is 10% dextran 40 (molecular weight 40,000) in 5% dextrose or in 0.9% NaCl.

Few toxic reactions have been observed when using either dextran or hetastarch for fluid replacement therapy.

The capillary wall is composed of a unicellular layer of endothelial cells and is surrounded by a basement membrane. The thickness of the wall is about 0.5 micron. The diameter of the capillary is 4 to 9 microns. The endothelial cells of the capillary wall are held apart approximately 6 to 7 nanometers (60 to 70 Angstroms) by pore-like structures. Most water-soluble ions and molecules pass between the interior and exterior of the capillary through these pores. Such substances include sodium and chloride ions, glucose etc.. If a substance is lipid-soluble, it can diffuse directly through the cell membranes without having to pass through the pores. Such substances include oxygen and carbon dioxide. The pores in the capillaries of some organs have special characteristics to meet the special needs of the organs. For example in the brain, the junctions between the capillary endothelial cells are in the main "tight" junctions that will allow only very small molecules to pass into the brain tissue. This is the so called blood-brain barrier. In the liver, the pores between the capillary endothelial cells are very wide so that almost all dissolved substances present in the plasma, including the plasma proteins can pass from the blood into the liver tissue. The pores of the intestinal membranes are midway between those of the muscles and the liver. The width of the capillary intercellular pores, 6 to 7 nanometers is about 20 times the diameter of the water molecule, which is the smallest molecule that normally passes through the capillary pores. On the other hand, the diameters of plasma protein molecules are slightly greater than the width of the pores. Other substances, such as sodium ions, chloride ions, glucose, and urea have intermediate diameters. The permeability of the capillary pores for different substances varies according to their molecular weights.

Methods for treating with the described compositions of the invention comprising one or more of the polysaccharides and in addition at least one other pharmacologic agent known to reduce the effects of trauma, inflammatory reactions, damage to endothelial cells and other tissues as well as agents known to enhance microcirculatory dynamics and reduce capillary permeability disclosed herein. The pharmacologically active agents include superoxide dismutase, catalase, glutathione peroxidase, hydroxyethyl rutoside, cyclic AMP and vitamin C. The compositions of the invention can be used as an adjunct in pre or post surgical procedures, shock syndromes, sepsis, burns, cardiovascular accidents, in transplant surgery, limb salvage, pancreatitis, ARDS, ischemic perfusion injuries, cancer radiation therapy, cancer immuno and chemotherapy, to prevent oxygen toxicity in hyperbaric oxygen therapy as well as in the numerous clinical conditions cited above.

The uncontrolled activity of free radicals (superoxide, singlet oxygen and the hydroxyls) results in damage to cells, tissues and organs. The study of free radical pathology has given us a better understanding of degenerative diseases, cancer and the aging process. Free radical pathology plays a part in immune-system suppression and susceptibility to infectious diseases. It is the extreme excitability of free radicals that makes them dangerous. They can destroy cell membranes causing cell fluid leakage and at the same time prevent the intake of cell nutrients.

Free radicals interact with DNA and RNA resulting in the production of mutations and may also cause uncontrolled fusion of large cell molecules (cross linking). The latter process is responsible for hardening of artery walls a factor in atherosclerosis and hypertension as well as effecting the aging process.

Admittedly, free radical activity under the proper control of the body serves many useful and essential functions. For example, the immune system can use potentially dangerous free radicals liberated by polymorphonuclear cells during inflammation. Similarly without controlled free radical reactions there would be no synthesis of prostaglandins that regulate many of our physiological functions.

However, given the threat to the integrity of cells from the uncontrolled activity of highly reactive species of free radicals it is critical that anti-oxidants be available to neutralize them.

The antioxidants used in this invention (superoxide dismutase, glutathione peroxidase, catalase, and cyclic adenosine monophosphate) are normally produced in the body but the amount available is dependent upon many circumstances and the concentration of these substances declines with age. Under ordinary circumstances anti-oxidants and vitamin co-factors are food derived; this is particularly true for vitamin C which is not produced in humans. They react one-on-one with free radicals, e.g., one molecule of beta-carotene can deactivate only one single oxygen radical and is used up in the process. Vitamin C twice as effective in that it can deactivate two free radicals.

More effective still are three enzyme systems: superoxide dismutase, catalase and glutathione peroxidase. In each system a single enzyme molecule can inactivate several thousand free radicals before the enzyme's protein structure breaks up. The functioning of the three enzyme systems is interconnected. In the process of deactivating superoxide, SOD will give rise to other free radicals which are then attacked by the enzyme catalase which specifically decomposes hydrogen peroxide, one of the most dangerous by products of the free radical process. Other challenges by free radicals are met by the third enzyme system, glutathione peroxidase, which uses available selenium an essential mineral nutrient.

Hydroxyethyl rutoside is a pharmacological agent which has been used clinically as an anti-edema agent and in inflammatory capillary hyperpermeability. The action of this agent appears to be as an anti-oxidant, specifically through inhibition of microsomal lipid peroxidation and thus membrane stabilization.

Cyclic adenosine monophosphate (cyclic AMP) influences many cellular processes. All known effects of cyclic AMP result from the activation of protein kinases. These kinases modulate the activities of different cellular proteins by phosphorylating them. Cyclic AMP is central to the coordinated control of glycogen synthesis and breakdown and thus the source of energy for cellular processes.

Vitamin C (ascorbic acid) is a powerful oxidation reduction agent and has been isolated in pure form and can be readily synthesized in large quantities. Vitamin C, besides its essential function in maintaining the integrity of connective tissue as well as being essential in the synthesis of collagen, is believed to function to prevent cancer on many different levels. It is a powerful antioxidant, blocking lipid peroxidation that would lead to free-radical formation. It is an immune enhancer and acts by stimulating the action of phagocytes, particularly macrophages. It may also stimulate the transformation of T and B cells and it appears to induce the body to manufacture more interferon. Vitamin C also acts as an antiviral. As there are a number of known cancer causing viruses, vitamin C may be an indirect preventer of cancers from such viruses.

The applicants have prepared compositions comprising a single polysaccharide macromolecule (hydroxyethyl starch or dextran) or both together in combination with an antioxidant(s). Compositions comprising a polysaccharide macromolecule and hydroxyethyl rutoside and in some preparations containing an additional antioxidant were also used by the inventors. Cyclic AMP and vitamin C was additionally included in many of the compositions.

The applicant has prepared various compositions of polysaccharide macromolecules and antioxidants and utilized them in order to inhibit or prevent capillary leakage and inflammatory changes before the trauma incident, for example extensive/major surgery or to correct or reduce the leakage after the trauma has occurred. The procedures carried out by the applicant have shown the following : reduction of the pathologic effects of trauma, reduction of the inflammatory reaction, reduction of damage to endothelial cells and other tissues, and enhancement of microcirculatory dynamics. These effects are realized as a consequence of the biophysical and biochemical properties of these molecules as endothelial junction stabilizers by positively effecting the osmotic balance between the intra (capillaries) and extra vascular space (interstitium) and by preventing the adverse effect of free radicals.

The applicants have recognized and appreciated these findings and have evaluated them in the treatment of central nervous system injury, such as stroke, ruptured aneurysm, brain injury, and spinal cord injury etc., in major trauma such as major surgery, limb salvage, burn injuries, poisonings (drug or snake venoms), in conditions such as pancreatitis, massive transfusions, anaphylaxis, sepsis, shock syndromes etc.

The total molecular weight range and composition of the final product may differ due to the fact that these macromolecules characteristically exhibit a wide range of molecular weights. The molecular weight ranges of the macromolecules used may also vary depending on the specific clinical application. For example compositions for use in treating cerebral trauma, a lower molecular range may be effective because the endothelial junctions of brain capillaries are considerably smaller than those in capillaries in other tissues.

Solutions of the macromolecules are prepared in 0.9% saline, 5% dextrose or Ringer'lactate, Ringer'lactate being the preferred carrier. The amount of the polysaccharide macromolecules in the compositions may vary but essentially range between 3–50%. The preferred concentration is 6–12%. The exact volume to be introduced intravenously is dependent on the specific clinical entity to be treated and the body weight of the subject. The usual volume is about 500 to 1500 mls (30–90 grams of polysaccharide in solution), however 1500 mls of 6% hydroxyethyl starch (90 grams) can readily be given to a 70 kg man over a 24 hour period. When the macromolecules are used in combination the total volume infused is similar to that used for a single macromolecule. The sum of the weight of macromolecules in the composition would be in the range of 3–50% and preferably between 6–12%, that is a total of 3–6 grams per 50 ml. Thus the composition would contain 1.5–3.0 grams of each of the component macromolecules per 50 ml if two are used in a 1:1 mixture. If used in a 4:1 mixture hydroxyethyl starch would be used as 2.4–4.8 grams to 0.6–1.2 grams of dextran per 50 mls.

Solutions of the polysaccharide molecules are made up in either 0.9% saline, 5% dextrose or Ringer'lactate. The usual volume given by intravenous injection is 500 to 1500 ml and contains about 6 to 12% polysaccharide macromolecules. For musculo-skeletal indications the hydroxyethyl starch should be of a molecular size ranging from 300 to 750 kilodaltons. Dextran should be used with an average molecular weight of 500 kilodaltons. Compositions for central nervous system treatment should contain hydroxyethyl starch with a molecular weight range of 150 to 400 kilodaltons. Dextran should be used with an average molecular weight of about 150 kilodaltons, but molecular weights of 40,000 could be used. Compositions for gastrointestinal pathology should contain macromolecules of greater molecular size, hydroxyethyl starch 500–750 kilodaltons and dextran 500 to 1500 kilodaltons. The amount of a single macromolecule when used would be 3–6 grams per 50 ml and the molecular size utilized would depend on the clinical condition dictating its use.

The anti-oxidants are included in the compositions, in the following concentrations: Superoxide dismutase, 5000–20,000 IU/kg per treatment; glutathione peroxidase 5–50 units/ml per treatment or 200–400 mg/kg; catalase 5000–12,500 IU/kg/treatment; hydroxyethyl rutoside 500–2,000 mg/70 kg person ; cyclic AMP 5–20 milimols/ml per treatment; and vitamin C 250–2,500 mgm/ al per treatment. The following examples are given in order to illustrate the invention and are not to be construed as limitative thereof.

In the examples of the compositions shown in the following table, concentrations for macromolecules are given for 20 ml/kg body weight.

| COMPOSITIONS | | | |
|---|---|---|---|
| polysaccharide | grams/ 20 ml | antioxidant | concentration |
| Hetastarch | 1.2 | superoxide dismutase | 5000–20,000 IU/kg |
| Dextran | 1.2 | superoxide dismutase | 5000–20,000 IU/kg |
| Hetast/Dextr | 0.6 + 0.6 | superoxide dismutase | 5000–20,000 IU/kg |
| Hetastarch | 1.2 | catalase | 5000–12,500 IU/kg |
| Dextran | 1.2 | catalase | 5000–12,500 IU/kg |
| Hetast/Dextr | 0.6 + 0.6 | catalase | 5000–12,500 IU/kg |
| Hetastarch | 1.2 | glutathione peroxidase | 200–400 mg/kg |
| Dextran | 1.2 | glutathione peroxidase | 200–400 mg/kg |
| Hetast/Dextr | 0.6 + 0.6 | glutathione peroxidase | 200–400 mg/kg |
| Hetastarch | 1.2 | vitamin C | 20–50 mg/kg |
| Hetastarch | 1.2 | vitamin C + glutathione peroxidase | 20–50 mg/kg 200–400 mg/kg |
| Hetast/Dextr | 0.6 + 0.6 | vitamin C | 20–50 mg/kg |
| Hetast/Dextr | 0.8 + 0.4 | vitamin C | 20–50 mg/kg |

Hetast means Hetastarch
Dext means Dextran

It should be understood that two or three of the enzymes can be present with either polysaccharide or with the combination of polysaccharides.

Cyclic adenosine monophosphate and/or vitamin C could be added to any of the compositions.

The compositions are prepared using either 6–12% hydroxyethyl starch or 6–12% dextran again dependent on the clinical indications. Molecular size of the polysaccharides are dictated by the clinical condition being treated. When using two polysaccharides they can be used in a ratio of 1 part hydroxyethyl starch to 1 part dextran up to 4:1 to 1:4. Macromolecules are always introduced intravenously. Treatment can be repeated as indicated.

The present invention provides a method of treating a human subject to prevent leakage of serum proteins from capillary endothelial junctions during a period of increased capillary permeability. The method also provides a method for preventing the harmful effects of free radicals on cellular membranes and other organelles. The method comprises administering to a subject an effective amount of a composition comprising at least one polysaccharide selected from the group consisting of hydroxyethyl starch and dextran of varying molecular sizes and at least one member of a group consisting of superoxide dismutase, glutathione peroxidase, catalase, hydroxyethyl rutoside, cyclic adenosine monophosphate and vitamin C. The compositions contain the macromolecules in a molecular size and concentration to effectively stabilize the capillary membrane. The stabilization effect is accomplished by a biophysical/biochemical process due to the adhesiveness and configuration of the macromolecules, and because of their size. The treatment is benign as the macromolecules and antioxidants are non-toxic and biodegradable.

We claim:

1. Method of treating a human subject to prevent leakage of serum proteins from capillary endothelial junctions while simultaneously preventing the harmful effect of free radicals on cellular membranes and other organelles during a period of increased capillary permeability which comprises administering to a subject in need of such treatment an effective amount of a composition comprising at least one polysaccharide selected from the group consisting of hydroxyethyl starch and dextran and at least one antioxidant selected from the group consisting of superoxide dismutase, glutathione peroxidase, catalase, hydroxyethyl rutoside, cyclic adenosine monophosphate and vitamin C, in admixture with a pharmaceutically acceptable liquid carrier.

2. Method according to claim 1 wherein said polysaccharide is hydroxyethyl starch.

3. Method according to claim 1 wherein said polysaccharide is dextran.

4. Method according to claim 1 wherein said polysaccharide is hydroxyethyl starch and dextran.

5. Method according to claim 1 wherein said antioxidant is superoxide dismutase.

6. Method according to claim 1 wherein said antioxidant is catalase.

7. Method according to claim 1 wherein said antioxidant is glutathione peroxidase.

8. Method according to claim 1 wherein said antioxidant is vitamin C.

9. Method according to claim 1 wherein said antioxidant is vitamin C and glutathione peroxidase.

10. Method according to claim 1 wherein said liquid carrier is a member selected from the group consisting of 0.9% saline, 5% dextrose and Ringer' lactate.

11. Method according to claim 1 wherein said polysaccharide is present in said composition in amount of about 3 to about 50%.

12. Method according to claim 1 wherein said polysaccharide is present in said composition in amount of about 6 to about 12%.

13. Method according to claim 1 wherein said composition is administered by intravenous injection in an amount of about 500 to 1500 ml per treatment.

14. Method according to claim 5 wherein said superoxide dismutase is administered in amount of about 5000 to about 20,000 IU/kg per treatment.

15. Method according to claim 6 wherein said catalase is administered in an amount of about 5000 to about 12,500 IU/kg per treatment.

16. Method according to claim 1 wherein said antioxidant is hydroxyethyl rutoside and is administered in an amount of about 500 to about 2000 mg/kg per treatment.

17. Method according to claim 1 wherein said antioxidant is cyclic AMP and is administered in an amount of about 5 to about 20 milimols/ml per treatment.

18. Method according to claim 8 wherein said antioxidant is vitamin C and is administered in amount of about 250 to about 2,500 mg/ml per treatment.

19. Method of treating a human subject to prevent leakage of serum proteins from capillary endothelial junctions during a period of increased capillary permeability and simultaneously preventing the harmful effects of free radicals on cellular membranes and other organelles which comprises intravenously administering to a subject in need of such treatment an effective amount of a composition comprising:

a) at least one polysaccharide consisting of hydroxyethyl starch and dextran and b) at least one antioxidant selected from the group consisting of superoxide dismutase, glutathione peroxidase, catalase, hydroxyethyl rutoside, cyclic adenosine monophosphate and vitamin C, in admixture with a pharmaceutically acceptable liquid carrier selected from the group consisting of 0.9% saline, 5% dextrose and Ringer' lactate and wherein said polysaccharide is present in an amount of about 6 to about 12%.

20. A composition for treating a human subject to prevent leakage of serum proteins from capillary endothelial junctions while simultaneously preventing the harmful effect of free radicals on cellular membranes and other organelles during a period of increased capillary permeability which comprises at least one polysaccharide selected from the group consisting of hydroxyethyl starch and dextran and at least one antioxidant selected from the group consisting of superoxide dismutase, glutathione peroxidase, catalase, hydroxyethyl rutoside, cyclic adenosine monophosphate and vitamin C, in admixture with a pharmaceutically acceptable liquid carrier.

* * * * *